United States Patent [19]

Sakizadeh et al.

[11] Patent Number: 5,369,000
[45] Date of Patent: Nov. 29, 1994

[54] POST-PROCESSING STABILIZERS FOR PHOTOTHERMOGRAPHIC ARTICLES

[75] Inventors: Kumars Sakizadeh, Woodbury; John T. Blair, Oakdale, both of Minn.; David T. Ask, Somerset, Wis.

[73] Assignee: Minnesota Mining and Manufacturing Company, St. Paul, Minn.

[21] Appl. No.: 54,850

[22] Filed: Apr. 29, 1993

[51] Int. Cl.⁵ .................. G03C 1/498; G03C 1/34
[52] U.S. Cl. ...................... 430/619; 430/607; 430/611
[58] Field of Search ................ 430/619, 607, 611

[56] References Cited

U.S. PATENT DOCUMENTS

| | | | |
|---|---|---|---|
| 3,180,731 | 4/1965 | Roman et al. | 96/29 |
| 3,457,075 | 7/1969 | Morgan et al. | 96/67 |
| 3,531,286 | 9/1970 | Renfrew | 96/67 |
| 3,589,903 | 6/1971 | Birkeland | 96/67 |
| 3,707,377 | 12/1972 | Tiers et al. | 96/114.1 |
| 3,761,270 | 9/1973 | deMauriac et al. | 96/67 |
| 3,764,329 | 10/1973 | Lee | 96/67 |
| 3,846,136 | 11/1974 | Sullivan | 96/114.1 |
| 3,874,946 | 4/1975 | Costa et al. | 96/48 HD |
| 3,994,732 | 11/1976 | Winslow | 96/114.1 |
| 4,021,249 | 5/1977 | Noguchi et al. | 96/114.1 |
| 4,022,617 | 5/1977 | Mcguckin | 96/29 D |
| 4,108,665 | 8/1978 | Gutman et al. | 96/114.1 |
| 4,128,557 | 12/1978 | Knight et al. | 260/299 |
| 4,137,079 | 1/1979 | Houle | 96/55 |
| 4,138,265 | 2/1979 | Shiao | 96/114.1 |
| 4,260,677 | 4/1981 | Winslow et al. | 430/618 |
| 4,451,561 | 5/1984 | Hirabayashi et al. | 430/619 |
| 4,452,885 | 6/1984 | Nozawa et al. | 430/614 |
| 4,460,681 | 7/1984 | Frenchik | 430/502 |
| 4,465,761 | 8/1984 | Takegawa et al. | 430/341 |
| 4,546,075 | 10/1985 | Kitaguchi et al. | 430/617 |
| 4,756,999 | 7/1988 | Swain et al. | 430/613 |
| 4,837,141 | 6/1989 | Kohno et al. | 430/559 |
| 4,883,747 | 11/1989 | Grieve et al. | 430/559 |

FOREIGN PATENT DOCUMENTS 5957234  9/1982  Japan.

OTHER PUBLICATIONS

*Research Disclosure* No. 29963, May 1989.
*Research Disclosure* No. 16977, May 1978.
*Research Disclosure* No. 16979, May 1978.
*Research Disclosure* No. 17029, Jun. 1978.
*Research Disclosure* No. 22812, Apr. 1983.
*Research Disclosure* No. 23419, Oct. 1983.
*The Theory of the Photographic Process*, 4th Ed., Macmillan Publishing Co., Inc., 1977, pp. 149–169.

*Primary Examiner*—Thorl Chea
*Attorney, Agent, or Firm*—Gary L. Griswold; Walter N. Kirn; Gregory A. Evearitt

[57] ABSTRACT

Post-processing stabilizers for photothermographic, silver imaging media are disclosed. The stabilizers are represented by the following general formulae:

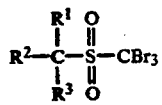

(I)

wherein: $R^1$, $R^2$, and $R^3$ are independently H, halogen, an alkyl group, an alkoxy group, a thioalkyl group, a cycloalkyl group, a perhalogenated alkyl group, or taken together form a cycloaliphatic group.

Compounds of formula (I) may be used as stabilizer precursors in photothermographic silver imaging media to provide post-processing stability without significantly adversely affecting desired properties of the photothermographic material.

7 Claims, No Drawings

POST-PROCESSING STABILIZERS FOR PHOTOTHERMOGRAPHIC ARTICLES

BACKGROUND OF THE ART

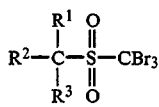

(I)

1. Field of Invention

This invention relates to photothermographic materials and in particular, it relates to post-processing stabilization of photothermographic silver-containing materials.

2. Background to the Art

Silver halide-containing photothermographic imaging materials processed with heat, and without liquid development, have been known in the art for many years. These materials generally comprise a support having thereon light-sensitive silver halide; a light-insensitive, organic silver salt; and a reducing agent for the light-insensitive organic silver salt.

The light-sensitive silver halide is in catalytic proximity to the light-insensitive organic silver salt so that the latent image, formed by irradiation of the silver halide, serves as a catalyst for the oxidation-reduction reaction of the light-insensitive, organic silver salt with the reducing agent when the emulsion is heated above about 80° C. Such media are disclosed, for example, in U.S. Pat. Nos. 3,457,075; 3,839,049; and 4,260,677.

A variety of ingredients may be added to these basic components to enhance performance. For example, toning agents may be incorporated to improve the color of the silver image of the photothermographic emulsions, as disclosed in U.S. Pat. Nos. 3,846,136; 3,994,732; and 4,021,249. Various methods to produce dye images and multicolor images with photographic color couplers and leuco dyes are disclosed in U.S. Pat. Nos. 4,022,617; 3,531,286; 3,180,731; 3,761,270; 4,460,681; 4,883,747; and Research Disclosure, March 1989, item 29963.

A common problem that exists with photothermographic systems is post-processing instability of the image. The photoactive silver halide still present in the developed image may continue to catalyze print-out of metallic silver during room light handling. Thus, there exists a need for stabilization of the unreacted silver halide. The addition of separate post-processing image stabilizers has been used to impart post-processing stability. Most often these are sulfur-containing compounds such as mercaptans, thiones, and thioethers as described in Research Disclosure, June, 1978, item 17029. U.S. Pat. Nos. 4,245,033; 4,837,141; and 4,451,561 describe sulfur compounds that are development restrainers for photothermographic systems. Mesoionic 1,2,4-triazolium-3-thiolates as fixing agents and silver halide stabilizers are disclosed in U.S. Pat. No. 4,378,424. Substituted 5-mercapto-1,2,4-triazoles such as 3-amino-5-benzothio-1,2,4-triazole as post-processing stabilizers are disclosed in U.S. Pat. Nos. 4,128,557; 4,137,079; 4,138,265; and Research Disclosure, May 1978, items 16977 and 16979.

Problems arising from the addition of stabilizers may include thermal fogging during processing and losses in photographic speed and maximum density or contrast at effective stabilizer concentrations.

The most effective traditional antifoggant has been mercuric ion as disclosed, for example, in U.S. Pat. No. 3,589,903. However, mercury compounds are environmentally undesirable and there is a need to find equally effective, but less hazardous antifoggants.

Various compounds have been used as antifoggants in place of mercury compounds in photothermographic silver imaging systems.

U.S. Pat. Nos. 3,707,377 and 4,108,665 disclose stabilization of thermally processed silver materials against formation of printout silver using a small amount of halogenated organic material, such as tribromoethanol. It is believed that photodecomposition of the halogenated organic compound generates bromine atoms, which combine with silver atoms from printout silver halide to maintain a low silver printout until the halogenated material is exhausted. The process can take years, though, depending on the amount of light exposure and the amount of halogenated material in the coating.

U.S. Pat. No. 3,764,329 uses N-bromoacetamide, an antifoggant, which has the oxidizing power of a halogen compound to bleach the latent image until it is time to use the light-sensitive material. The light sensitivity is achieved by brief heating to destroy the N-bromoacetamide used.

U.S. Pat. No. 3,874,946 describes a stabilizer precursor comprising a compound, which is a photolytically active polybrominated organic compound comprising: (a) a 2,4-bis(tribromomethyl)-s-triazine, (b) a polybromoalkylsulfonyl compound having an aromatic chromophore group having the ability to absorb electromagnetic radiation with a wavelength between about 250 and 385 nm, or (c) combinations thereof in a photothermographic element or composition. A preferred stabilizer disclosed in this Patent is 2-tribromomethyl-sulfonyl-benzothiazole (2-TBMBz).

U.S. Pat. No. 4,546,075 discloses, as antifoggants in place of mercury. compounds, the use of trihalomethyl-tetrazole derivatives, trihalomethyl-benzimidazoles, and corresponding benzoxazoles and benzthiazoles.

Japanese published Pat. Appl. No. 59-57234 discloses, as antifoggants in place of mercury compounds in photothermographic silver systems, the use of compounds of the formula:

wherein: X represents halogen, preferably Br, and $R^a$ and $R^b$ are optionally substituted acyl, oxycarbonyl, oxysulfonyl, alkylsulfonyl, arylsulfonyl, aralkylsulfonyl, carboxyl, sulfo, or sulfamoyl.

U.S. Pat. No. 4,465,761 discloses the use of organohalogen compounds, including compounds of the formula:

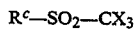

wherein: X represents halogen and $R^c$ is an aryl group, an alkyl group, allyl, or a heterocyclic residue. The materials are used in a non-silver photosensitive composition in which the organohalogen compounds are capable of forming a free-radical by the irradiation with light.

U.S. Pat. No. 4,452,885 discloses, as antifoggants in place of mercury compounds, the use of 2-trihalomethyloxazole derivatives.

U.S. Pat. No. 4,756,999 discloses as antifoggants in place of mercury compounds, the use of various heterocyclic systems bearing trihalomethyl functionality.

SUMMARY OF THE INVENTION

An alternative group of compounds has now been found which are effective antifoggants in photothermographic elements and which provide certain advantages over the use of both mercury antifoggants and the organic antifoggants of the prior art.

The inventive compounds can be represented by the following formula:

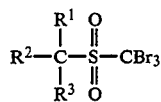  (I)

wherein: $R^1$, $R^2$, and $R^3$ are independently H, halogen, an alkyl group, an alkoxy group, a thioalkyl group, a cycloalkyl group, a perhalogenated alkyl group, or taken together form a cycloaliphatic ring, preferably a 5, 6, or 7-membered ring. Preferably, $R^1$, $R^2$, and R3 are independently bromine or an alkyl group, and most preferably, are bromine or $-(CH_2)_ySO_2CBr_3$ wherein y is an integer of from 0 to 22 inclusive; preferably from 2 to 7 inclusive; and most preferably is 2.

In a preferred embodiment, the present invention provides novel post-processing stabilizers having the following formulae:

  (II)

wherein n is an integer of 1 to 22 inclusive; preferably from 2 to 6 inclusive: and most preferably is 2; and

  (III)

wherein y is defined as above.

In another embodiment, the present invention provides photothermographic articles comprising a photothermographic composition coated on a substrate wherein the photothermographic composition comprises: light-sensitive silver halide; a light-insensitive organic silver salt; a reducing agent for the light-insensitive organic silver salt; and an antifoggant or stabilizer of formula (I) disclosed earlier herein, and preferably of formulae (II) or (III), as disclosed earlier herein.

As is well understood in this technical area, a large degree of substitution is not only tolerated, but is often advisable. As a means of simplifying the discussion and recitation of these groups, the terms "group" and "radical" are used to differentiate between chemical species that allow for substitution or which may be substituted. For example, the phrase "alkyl group" is intended to include not only pure hydrocarbon alkyl chains such as methyl, ethyl, octyl, cyclohexyl, isooctyl, tertbutyl and the like, but also such alkyl chains bearing such conventional substituents in the art such as hydroxyl, alkoxy, phenyl, halo (F, Cl, Br, I), cyano, nitro, amino, etc., and heteroatoms such as O, N, and S. The phrase "alkyl radical" on the other hand is limited to the inclusion of only pure hydrocarbon alkyl chains such as methyl, ethyl, propyl, cyclohexyl, isooctyl, tert-butyl, and the like.

The stabilizers of the present invention may be employed in photothermographic silver imaging media to provide post-processing stability without significantly or adversely affecting sensitometric properties of the photothermographic material.

In addition, compounds of formulae (I), (II), and (III) may be used as photoinitiators in photopolymerization reactions or as brominated oxidizing agents in organic reactions.

Other aspects, advantages, and benefits of the present invention are apparent from the detailed description, examples, and claims.

DETAILED DESCRIPTION OF THE INVENTION

In one embodiment, the present invention provides novel, post-processing stabilizers or antifoggants of the following formula:

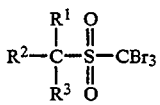  (I)

wherein: $R^1$, $R^2$, and $R^3$ are independently H, halogen, an alkyl group, a alkoxy group, a thioalkyl group, a cycloalkyl group, a perhalogenated alkyl group, or taken together form a cycloaliphatic ring, preferably a 5, 6, or 7-membered ring.

Preferably, $R^1$, $R^2$, arid $R^3$ are independently bromine or an alkyl group, and most preferably, are bromine or $-(CH_2)_ySO_2CBr_3$ wherein y is an integer of from 0 to 22 inclusive; preferably from 2 to 7 inclusive; and most preferably is 2.

In a preferred embodiment, the present invention provides novel post-processing stabilizers of the following formulae:

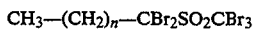  (II)

wherein n is an integer of 1 to 22 inclusive; preferably from 2 to 6 inclusive; and most preferably is 2; and

  (III)

wherein y is as defined earlier herein.

The foregoing compounds (I), (II), and (III) can be synthesized according to procedures of synthetic organic chemistry known to those skilled in the art and as described later herein.

In another embodiment, the present invention provides photothermographic articles comprising a photothermographic composition coated on a substrate wherein the photothermographic construction comprises: light-sensitive silver halide; a light-insensitive organic silver salt; a reducing agent for the light-insensitive organic silver salt; and a post-processing stabilizer having the formula (I) and preferably, (II) or (III), as disclosed earlier herein.

In photothermographic articles of the present invention the layer(s) that contain the photosensitive silver halide are referred to herein as emulsion layer(s). According to the present invention the post-processing stabilizer is added either to one or more emulsion layers or to a layer or layers adjacent to one or more emulsion layers. Layers that are adjacent to emulsion layers may be for example, primer layers, image-receiving layers, interlayers, opacifying layers, antihalation layers, barrier layers, auxiliary layers, etc.

Photothermographic articles of the present invention may contain other post-processing stabilizers or stabilizer precursors in combination with the compounds of the invention, as well as other additives, as shelf-life stabilizers, toners, development accelerators, and other image-modifying agents.

The amounts of the above-described ingredients that are added to the emulsion layer according to the present invention may be varied depending upon the particular compound used and upon the type of emulsion layer (i.e., black and white or color). However, the ingredients are preferably added in an amount of 0.01 to 100 mol, and more preferably from 0.1 to 50 mol, per mol of silver halide in the emulsion layer.

The light sensitive silver halide used in the present invention may typically be employed in a range of 0.75 to 25 tool percent and, preferably from 2 to 20 mol percent, of organic silver salt.

The silver halide may be any light-sensitive silver halide such as silver bromide, silver iodide, silver chloride, silver bromoiodide, silver chlorobromoiodide, silver chlorobromide, etc. The silver halide may be in any form which is photosensitive including, but not limited to cubic, orthorhombic, tabular, tetrahedral, etc., and may have epitaxial growth of crystals thereon.

The silver halide used in the present invention may be employed without modification. However, it may be chemically sensitized with a chemical sensitizing agent such as a compound containing sulfur, selenium or tellurium ,etc. or a compound containing gold, platinum, palladium, rhodium or iridium, etc., a reducing agent such as a tin halide, etc., or a combination thereof. The details of these procedures are described in T. N. James, *The Theory of the Photographic Process*, Fourth Edition, Chapter 5, pages 149 to 169.

The silver halide may be added to the emulsion layer in any fashion which places it in catalytic proximity to the silver source. Silver halide and the organic silver salt which are separately formed or "preformed" in a binder can be mixed prior to use to prepare a coating solution, but it is also effective to blend both of them in a ball mill for a long period of time. Further, it is effective to use a process which comprises adding a halogen-containing compound in the organic silver salt prepared to partially convert the silver of the organic silver salt to silver halide.

Methods of preparing these silver halide and organic silver salts and manners of blending them are known in the art and described in *Research Disclosure*, June 1978, item 17029, and U.S. Pat. No. 3,700,458.

The use of preformed silver halide emulsions of this invention can be unwashed or washed to remove soluble salts. In the latter case the soluble salts can be removed by chill-setting and leaching or the emulsion can be coagulation washed for example, by the procedures described in U.S. Pat. Nos. 2,618,556; 2,614,928; 2,565,418; 3,241,969; and 2,489,341. The silver halide grains may have any crystalline structure, including, but not limited to cubic, tetrahedral, orthorhombic, tabular, laminar, platelet, etc.

The organic silver salt may be any organic material which contains a reducible source of silver ions. Silver salts of organic acids, particularly long chain (10 to 30, preferably 15 to 28, carbon atoms), fatty carboxylic acids are preferred. Complexes of organic or inorganic silver salts wherein the ligand has a gross stability constant between 4.0 and 10.0 are also desirable. The silver source material should preferably constitute from about 5 to 30 percent by weight of the imaging layer.

The organic silver salt which can be used in the present invention is a silver salt which is comparatively stable to light, but forms a silver image when heated to 80° C. or higher in the presence of an exposed photocatalyst (such as photographic silver halide) and a reducing agent.

Preferred organic silver salts include silver salts of organic compound is having a carboxyl group. Nonlimiting examples thereof include silver salts of an aliphatic carboxylic acid and a silver salt of an aromatic carboxylic acid. Preferred examples of the silver salts of aliphatic carboxylic acids include silver behenate, silver stearate, silver oleate, silver laurate, silver caproate, silver myristate, silver palmitate, silver maleate, silver fumarate, silver tartrate, silver linoleate, silver butyrate, and silver camphorate, and mixtures thereof, etc. Silver salts with a halogen atom or an —OH on the aliphatic carboxylic acid can also be effectively used. Preferred examples of the silver salts of aromatic carboxylic acids and other carboxyl group-containing compounds include silver benzoate, a silver substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc., silver gallate, silver tannate, silver phthalate, silver terephthalate, silver salicylate, silver phenylacetate, silver salts of 3-carboxymethyl-4-methyl-4-thiazoline-2-thiones or the like as described in U.S. Pat. No. 3,785,830 and silver salts of aliphatic carboxylic acids containing a thioether group as described in U.S. Pat. No. 3,330,663.

Silver salts of compounds containing mercapto or thione groups and derivatives thereof can also be used. Preferred examples of these compounds include silver 3-mercapto-4-phenyl-1,2,4-triazolate, silver 2-mercaptobenzimidazolate, silver 2-mercapto-5-aminothiadiazolate, silver 2-(ethylglycolamido)benzothiazolate, silver thioglycolates such as silver S-alkyl thioglycolates (wherein the alkyl group has from 12 to 22 carbon atoms), silver dithiocarboxylates such as silver dithioacetate, silver thioamidate, silver 1-methyl-2-phenyl-4-thiopyridine-5-carboxylate, silver triazinethiolate, silver salts of 2-sulfidobenzoxazoles, silver salts as described in U.S Pat. No. 4,123,274, for example, silver salts of 1,2,4-mercaptothiazole derivative such as silver 3-amino-5-benzylthio-1,2,4-thiazolate, and silver salts of thione compounds such as silver 3-(2-carboxylatoethyl)-4-methyl-4-thiazoline-2-thione as disclosed in U.S. Pat. No. 3,301,678.

Furthermore, silver salts of compounds containing an imino group may be used. Preferred examples of these compounds include silver salts of benzothiazole and derivatives thereof, for example, silver methylbenzotriazolate, etc., silver salts of halogen-substituted benzotriazoles, such as silver 5-chlorobenzotriazolate, etc., silver salts of carboimidobenzotriazole, etc., silver salts of 1,2,4-triazoles or 1H-tetrazoles as described in U.S. Pat. No. 4,220,709, silver salts of imidazoles and imidazole derivatives, and the like. Various silver acetylide compounds can also be used as described, for example, in U.S. Pat. Nos. 4,761,361 and 4,775,613.

It is also found convenient to use silver half soaps, of which an equimolar blend of silver behenate and behenic acid, prepared by precipitation from aqueous solution of the sodium salt of commercial behenic acid and analyzing about 14.5 percent silver, represents a preferred example. Transparent sheet materials made on transparent film backing require a transparent coating and for this purpose the silver behenate full soap, containing not more than about 4 or 5 percent of free behenic acid and analyzing about 25.2 percent silver, may be used.

The method used for making silver soap dispersions is well known in the art and is disclosed in *Research Disclosure*, April 1983, item 22812, *Research Disclosure*, October 1983, item 23419 and U.S. Pat. No. 3,985,565.

The light-sensitive silver halides may be advantageously spectrally sensitized with various known dyes including cyanine, merocyanine, styryl, hemicyanine, oxonol, hemioxonol, and xanthene dyes. Useful cyanine dyes include those having a basic nucleus, such as a thiazoline nucleus, an oxazoline nucleus, a pyrroline nucleus, a pyridine nucleus, an oxazole nucleus, a thiazole nucleus, a selenazole nucleus, and an imidazole nucleus. Useful merocyanine dyes which are preferred include those having not only the above-described basic nuclei, but also acid nuclei, such as a thiohydantoin nucleus, a rhodanine nucleus, an oxazolidinedione nucleus, a thiazolidinedione nucleus, a barbituric acid nucleus, a thiazolinone nucleus, a malonitrile nucleus, and a pyrazolone nucleus. In the above-described cyanine and merocyanine dyes, those having imino groups or carboxyl groups are particularly effective. Practically, the sensitizing dyes to be used in the present invention may be properly selected from known dyes such as those described in U.S. Pat. Nos. 3,761,279; 3,719,495; 3,877,943; and British Pat. Nos. 1,466,201; 1,469,117; and 1,422,057, and can be located in the vicinity of the photocatalyst according to known methods. Spectral sensitizing dyes may be typically used in amounts of about $10^{-4}$ mole to about 1 mole per mole of photocatalyst.

The reducing agent for the organic silver salt may be any material, preferably organic material, that can reduce silver ion to metallic silver. Conventional photographic developers such as phenidone, hydroquinones, and catechol are useful, but hindered phenol reducing agents are preferred. The reducing agent should be prevent as 1 to 10 percent by weight of the imaging layer. In multilayer constructions, if the reducing agent is added to a layer other than an emulsion layer, slightly higher proportions, of from about 2 to 15 percent, tend to be more desirable.

A wide range of reducing agents has been disclosed in dry silver systems including amidoximes such as phenylamidoxime, 2-thienylamidoxime and p-phenoxyphenylamidoxime, azines (e.g., 4-hydroxy-3,5-dimethoxybenzaldehydeazine); a combination of aliphatic carboxylic acid aryl hydrazides and ascorbic acid, such as 2,2'-bis(hydroxymethyl)propionylbetaphenyl hydrazide in combination with ascorbic acid; a combination of polyhydroxybenzene and hydroxylamine, a reductone and/or a hydrazine, e.g., a combination of hydroquinone and bis(ethoxyethyl)hydroxylamine, piperidinohexose reductone or formyl-4-methylphenylhydrazine, hydroxamic acids such as phenylhydroxamic acid, p-hydroxyphenylhydroxamic acid, and o-alaninehydroxamic acid; a combination of azines and sulfonamidophenols, e.g., phenothiazine and 2,6-dichloro-4-benzenesulfonamidophenol; α-cyano-phenylacetic acid derivatives such as ethyl α-cyano-2-methylphenylacetate, ethyl α-cyano-phenylacetate; bis-o-naphthols as illustrated by 2,2'-dihydroxyl-1-binapht-hyl, 6,6'-dibromo-2,2'-dihydroxy-1,1'-binaphthyl, and bis(2-hydroxy-1-naphthyl)methane; a combination of bis-o-naphthol and a 1,3-dihydroxybenzene derivative, (e.g., 2,4-dihydroxybenzophenone or 2,4-dihydroxyacetophenone); 5-pyrazolones such as 3-methyl-1-phenyl- 5-pyrazolone; reductones as illustrated by dimethylaminohexose reductone, anhydrodihydroaminohexose reductone, and anhydrodihydro-piperidone-hexose reductone; sulfonamidophenol reducing agents such as 2,6-dichloro-4-benzene-sulfonamidophenol, and p-benzenesulfonamidophenol; 2-phenylindane-1,3-dione and the like; chromans such as 2,2-dimethyl-7-t-butyl-6-hydroxychroman; 1,4-dihydropyridines such as 2,6-dimethoxy-3,5-dicarbethoxy-1,4-dihydropyridine; bisphenols, e.g., bis(2-hydroxy-3-t-butyl-5-methylphenyl)methane; 2,2-bis(4-hydroxy-3-methylphenyl)-propane; 4,4-ethylidene-bis(2-t-butyl-6-methylphenol); and 2,2-bis(3,5-dimethyl-4-hydroxyphenyl)propane; ascorbic acid derivatives, e.g., 1-ascorbylpalmitate, ascorbylstearate and unsaturated aldehydes and ketones, such as benzyl and diacetyl; 3-pyrazolidones; and certain indane-1,3-diones.

In addition to the aforementioned ingredients it may be advantageous to include additives known as "toners" that improve the image. Toner materials may be present, for example, in amounts from 0.1 to 10 percent by weight of all silver bearing components. Toners are well known materials in the photothermographic, art as shown in U.S. Pat. Nos. 3,080,254; 3,847,612; and 4,123,282.

Examples of toners include phthalimide and N-hydroxyphthalimide; cyclic imides such as succinimide, pyrazoline-5-ones, and a quinazolinone, 3-phenyl-2-pyrazoline-5-one, 1-phenylurazole, quinazoline, and 2,4-thiazolidinedione; naphthalimides (e.g., N-hydroxy-1,8-naphthalimide); cobalt complexes (e.g., cobaltic hexamine trifluoroacetate); mercaptans as illustrated by 3-mercapto-1,2,4-triazole, 2,4-dimercaptopyrimidine, 3-mercapto-4,5-diphenyl-1,2,4-triazole and 2,5-dimer-capto-1,3,4-thiadiazole; N-(aminomethyl)aryldicarboximides, e.g. (N,N-dimethylaminomethyl)phthalimide and N,N-(dimethylaminomethyl)naphthalene-2,3-dicarboximide; and a combination of blocked pyrazoles, isothiuronium derivatives and certain photobleaching agents (e.g., a combination of N,N'-hexamethylene-bis(1-carbamoyl-3,5-dimethylpyrazole), 1,8-(3,6-diazaoctane)bis(isothiuronium trifluoroacetate) and 2-(tribromomethylsulfonyl)benzothiazole; and merocyanine dyes such as 3-ethyl-5-[(3-ethyl-2-benzothiazolinylidene)-1-methylethylidene]-2-thio-2,4-oxazolidinedione; phthalazinone and phthalazinone derivatives or metal salts or these derivatives such as 4-(1-naphthyl)phthalazinone, 6-chlorophthalazinoine, 5,7-dimethoxyphthalazinone, and 2,3-dihydro-1,4-phthalazinedione; a combination of phthalazinone plus sulfinic acid derivatives (e.g., phthalic acid, 4-methylphthalic acid, 4-nitrophthalic acid, and tetrachlorophthalic anhydride); quinazolinediones, benzoxazine or naphthoxazine derivatives; rhodium complexes functioning not only as tone modifiers, but also as sources of halide ion for silver halide formation in situ, such as ammonium hexachlororhodate (III), rhodium bromide, rhodium nitrate, and potassium hexachlororhodate (III); inorganic peroxides and persulfates (e.g., ammonium peroxydisulfate and hydrogen peroxide); benzoxazine-2,4-diones such as 1,3-benzoxazine-2,4-dione,8-methyl-1,3-benzoxazine-2,4-dione, and 6-nitro-1,3-benzoxazine-2,4-dione; pyrimidines and asymmetric triazines, e.g., 2,4-dihydroxypyrimidine, 2-hydroxy-4-aminopyrimidine, and azauracil, and tetraza-pentalene derivatives, e.g., 3,6-dimercapto- 1,4-diphenyl-1 H, 4H-2,3a,5,6a-tetrapentalene, and 1,4-di(o-chlorophenyl)-3,6-dimercapto-1H,4H-2,3a,5,6a-tetraza-pentalene.

A number of methods are known in the art for obtaining color images with dry silver systems including: a combination of silver benzotriazole, well known magenta, yellow, and cyan dye-forming couplers, aminophenol developing agents, a base release agent such as guanidinium trichloroacetate and silver bromide in poly(vinyl butyral) as described in U.S. Pat. Nos. 4,847,188 and 5,064,742; preformed dye release systems such as those described in U.S. Pat. No. 4,678,739; a combination of silver bromoiodide, sulfonamidophenol reducing agent, silver behenate, poly(vinyl butyral), an amine such as n-octadecylamine and 2-equivalent or 4-equivalent cyan, magenta or yellow dye-forming couplers; leuco dye bases which oxidize to form a dye image (e.g., Malachite Green, Crystal Violet and pararosaniline); a combination of in situ silver halide, silver behenate, 3-methyl-1-phenylpyrazolone and N,N'-dimethyl-p-phenylenediamine hydrochloride; incorporating phenolic leuco dye reducing agents such as 2(3,5-di-(t-butyl)-4-hydroxyphenyl)-4,5-diphenylimidazole, and bis(3,5-di-(t-butyl)-4-hydroxyphenyl)phenylmethane, incorporating azomethine dyes or azo dye reducing agents; and silver dye bleach processes. For example, an element comprising silver behenate, behenic acid, poly(vinyl butyral), poly(vinyl butyral) peptized silver bromoiodide emulsion, 2,6-dichloro-4-benzenesulfonamido-phenol-1,8-(3,6-diazaoctane)bis-isothiuronium-p-toluenesulfonate and an azo dye was exposed and heat processed to obtain a negative silver image with a uniform distribution of dye which was laminated to an acid activator sheet comprising polyacrylic acid, thiourea, and p-toluenesulfonic acid and heated to obtain a well-defined positive dye image. Also useful are amines such as aminoacetanilide (yellow dye-forming), 3,3'-dimethoxybenzidine (blue dye-forming), or sulfanilanilide (magenta dye forming) that react with the oxidized form of incorporated reducing agents such as 2,6-dichloro-4-benzenesulfonamidophenol to form dye images. Neutral dye images can be obtained by the addition of amines such as behenylamine and p-anisidine.

Leuco dye oxidation in such silver halide systems for color formation is disclosed in U.S. Pat. Nos. 4,021,240, 4,374,821, 4,460,681, and 4,883,7471.

Silver halide emulsions containing the stabilizers of this invention can be protected further against the additional production of fog and can be stabilized against loss of sensitivity during shelf storage. Suitable antifoggants, stabilizers, and stabilizer precursors which can be used alone or in combination, include thiazolium salts as described in U.S. Pat. Nos. 2,131,038 and 2,694,716; azaindenes as described in U.S. Pat. Nos. 2,886,437 and 2,444,605; mercury salts as described in U.S. Pat. No. 2,728,663; urazoles as described in U.S. Pat. No. 3,287.13.5; sulfocatechols as described in U.S. Pat. No. 3,235,652; oximes as described in British Pat. No. 623,448; nitrones; nitroindazoles; polyvalent metal salts as described in U.S. Pat. No. 2,839,405; thiouronium salts as described in U.S. Pat. No. 3,220,839; and palladium, platinum and gold salts described in U.S. Pat. Nos. 2,566,263 and 2,597,915; halogen-substituted organic compounds as described in U.S. Pat. Nos. 4,108,665 and 4,442,202; triazines as described in U.S. Pat. Nos. 4,128,557; 4,137,079; 4,138,265; and 4,459,350; and phosphorus compounds as described in U.S. Pat. No. 4,411,985.

Stabilized emulsions of the invention can contain plasticizers and lubricants such as polyalcohols, e.g., glycerin and diols of the type described in U.S. Pat. No. 2,960,404; fatty acids or esters such as those described in U.S. Pat. No. 2,588.765 and U.S. Pat. No. 3,121,060; and silicone resins such as those described in British Pat. No. 955,061.

The photothermographic elements of the present invention may include image dye stabilizers. Such image dye stabilizers are illustrated by British Pat. No. 1,326,889; and U.S. Pat. Nos. 3,432,300; 3,698,909; 3,574,627; 3,573,050; 3,764,337 and 4,042,394.

Photothermographic elements containing emulsion layers stabilized according to the present invention can be used in photographic elements which contain light absorbing materials and filter dyes such as those described in U.S. Pat. Nos. 3,253,921; 2,274,782; 2,527,583; and 2,956,879. If desired, the dyes can be mordanted, for example, as described in U.S. Pat. No. 3,282,699.

Photothermographic elements containing emulsion layers stabilized as described herein can contain matting agents such as starch, titanium dioxide, zinc oxide, silica, and polymeric beads including beads of the type described in U.S. Pat. Nos. 2,992,101 and 2,701,245.

Emulsions stabilized in accordance with this invention can be used in photothermographic elements which contain antistatic or conducting layers, such as layers that comprise soluble salts, e.g., chlorides, nitrates, etc., evaporated metal layers, ionic polymers such as those described in U.S. Pat. Nos. 2,861,056 and 3,206,312 or insoluble inorganic salts such as those described in U.S. Pat. No. 3,428,451.

The photothermographic dry silver emulsions of this invention may be constructed of one or more layers on a substrate. Single layer constructions should contain the silver source material, the silver halide, the developer, and binder as well as optional materials such as toners, coating aids, and other adjuvants. Two-layer constructions should contain the silver source and silver halide in one emulsion layer (usually the layer adjacent to the substrate) and some of the other ingredients in the second layer or both layers, although two layer constructions comprising a single emulsion layer coating containing all the ingredients and a protective topcoat are envisioned. Multicolor photothermographic dry silver constructions may contain sets of these bilayers for each color or they may contain all ingredients within a single layer as described in U.S. Pat. No. 4,708,928. In the case of multilayer, multicolor photothermographic articles, the various emulsion layers are generally maintained distinct from each other by the use of functional or non-functional barrier layers between the various photosensitive layers as described in U.S. Pat. No. 4,460,681.

The binder may be selected from any of the well known natural or synthetic resins such as gelatin, polyvinyl acetals, polyvinyl chloride, polyvinyl acetate, cellulose acetate, polyolefins, polyesters, polystyrene, polyacrylonitrile, polycarbonates, and the like. Copolymers and terpolymers of the foregoing are, of course, included. The preferred photothermographic silver-containing polymers are polyvinyl butyral, butylethyl cellulose, methacrylate copolymers, maleic anhydride ester copolymers, polystyrene, and butadiene-styrene copolymers.

Optionally, these polymers may be used in combinations of two or more thereof. Such a polymer is used in an amount sufficient to carry the components dispersed therein, i.e., that is, within the effective range of the action as the binder. The effective range can be appropriately determined by one skilled in the art. As a guide in the case of utilizing at least an organic silver salt, it can be said that a preferable ratio of the binder to the organic silver salt ranges from 15:1 to 1:2, and particularly from 8:1 to 1:1 by weight.

Photothermographic emulsions containing a stabilizer according to the present invention may be coated on a wide variety of supports. Typical supports include polyester film, subbed polyester film, polyethylene terephthalate film, cellulose nitrate film, cellulose ester film, polyvinyl acetal film, polycarbonate film and related or resinous materials, as well as glass, paper metal and the like. Typically, a flexible support is employed, especially a paper support, which may be partially acetylated or coated with baryta and/or an α-olefin polymer, particularly a polymer of an α-olefin containing 2 to 10 carbon atoms such as polyethylene, polypropylene, ethylenebutene copolymers and the like. Substrates may be transparent or opaque.

Substrates with a backside resistive heating layer may also be used in color photothermographic imaging systems such as disclosed in U.S. Pat. Nos. 4,460,681 and 4,374,921.

Photothermographic emulsions of this invention can be coated by various coating procedures including dip coating, air knife coating, curtain coating, or extrusion coating using hoppers of the type described in U.S. Pat. No. 2,681,294. If desired, two or more layers may be coated simultaneously by the procedures described in U.S. Pat. No. 2,761,791 and British Pat. No. 837,095.

Additional layers may be incorporated into photothermographic articles of the present invention such as dye receptive layers for receiving a mobile dye image, an opacifying layer when reflection prints are desired, a protective topcoat layer, and a primer layer as is known in the photothermographic an. Additionally, it may be desirable in some instances to coat different emulsion layers on both sides of a transparent substrate, especially when it is desirable to isolate the imaging chemistries of the different emulsion layers.

The following non-limiting examples further illustrate the present invention.

EXAMPLES

All materials used in the following examples were readily available from standard commercial sources such as Aldrich Chemical Co. (Milwaukee, Wis.) unless otherwise noted. All stabilizers were characterized by one or more of the following techniques: melting point, $^1$H- and $^{13}$C-nuclear magnetic resonance spectroscopy, and infrared spectroscopy. Butvar TM refers to polyvinylbutyral resins available from Monsanto, St. Louis, Mo.

Dye-1 was prepared according to the procedure disclosed in JP-302558 and has the formula:

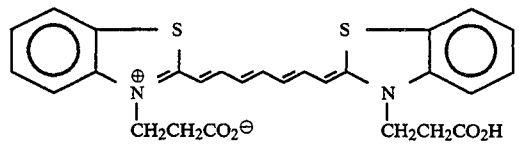

Dye-2 was prepared according to the procedure disclosed in U.S. Pat. No. 3,719,495 and has the formula:

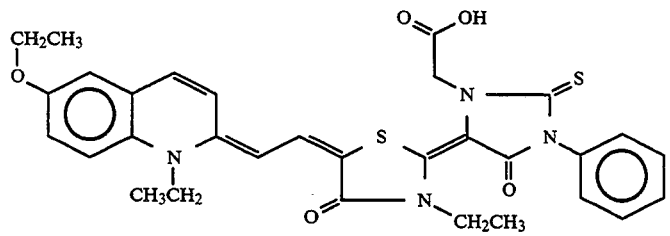

General Procedure for the Preparation of Stabilizers of Formula (II)

Mercaptoacetic acid (12.04 g, 0.13 mol) was added dropwise into a well-stirred solution of a 1-bromoalkane (0.12 mol) and sodium bicarbonate (25.20 g, 0.3 mol) in a mixture of water (100 ml) and ethanol (100 ml). The reaction mixture was then subjected to reflux condition for 8 hours. The resulting mixture was kept in an ice bath and acidified with conc. HCl to pH = 1. The resulting (typically waxy) material was filtered off, washed with water, and dried in a vacuum oven to give the corresponding thioether acetate in high yield.

Bromine (63.9 g, 0.40 mol) was added dropwise into a solution of sodium hydroxide (33.0 g, 0.825 mol) in water (200 ml) kept in an ice/salt bath at a rate which maintained the temperature below 10° C. The reaction mixture was kept stirring at 5°–10° C. for 30–40 minutes. At the same time the above was being completed, a slurry of the thioether obtained from the first step (0.05 mol) in water (160 ml) was prepared in a beaker. To this was added sodium bicarbonate (5.14 g, 0.06 mol) in a portion-wise manner to avoid foaming. After stirring for about 40 minutes, the mixture was filtered to give a clear solution. This solution was then added dropwise into the Br$_2$/NaOH/H$_2$O solution described earlier at a rate which maintained temperatures under 15° C. After the addition was completed, the stirring was continued for overnight to give a white precipitate that was filtered, washed width water, and air-dried.

General Procedure for the Preparation of Stabilizers of Formula (III)

Mercaptoacetic acid (20.26 g, 0.22 mol) was added dropwise into a well-stirred solution of αω-dibromohydrocarbon (0.1 mol) and sodium bicarbonate (42.0 g, 0.5 mol) in a mixture of water (200 ml) and ethanol (200 ml). The reaction mixture was then heated at reflux for 16 hours. Upon cooling, the reaction mixture was placed in an ice bath, and was acidified with concentrated hydrochloric acid to pH=1. The resulting (typically white) dithioether precipitated, was collected by filtration, washed with water, and dried in a vacuum oven at 60° C.

Bromine (127.8 g, 0.80 mol) was added dropwise into a solution of sodium hydroxide (66.0 g, 1.65 mol) in water (400 ml) kept in an ice/salt bath at a rate which maintained the temperature below 10° C. The reaction mixture was kept stirring at 5°–10° C. for 30–40 minutes. Simultaneously, a slurry of the dithioether obtained from the first step (0.05 mol) in water (300 ml) was prepared in a beaker. To this was added sodium bicarbonate (10.31 g, 0.123 mol) in a portion-wise manner to avoid foaming. After stirring for about 40 minutes, the mixture was filtered to give a clear solution. This solution was then added dropwise into the $Br_2/NaOH/H_2O$ solution described earlier at a rate which maintained temperatures under 20° C.

After the addition was completed, the stirring was continued for another 4–6 hours while the reaction mixture was kept in ice bath. The white precipitate was filtered, washed with water, and air-dried following by drying in a vacuum oven at 50° C.

Preparation of Stab.-6 and Stab.- 13

Bis(tribromomethyl)sulfone (Stab.-6) was prepared by the addition of dimethyl sulfoxide into a solution of sodium hypobromite at a temperature below 10° C.

2-Bromobutane-2-tribromomethylsulfone (Stab.-13) was prepared by the addition of sodium iso-butylthioacetate into a solution hypobromite. Sodium iso-butylthioacetate was prepared by reaction of 2-bromobutane with mercaptoacetic acid.

TABLE 1

STABILIZERS PREPARED AND TESTED

| STRUCTURE | ABBREVIATION |
|---|---|
| $CH_3(CH_2)_2CBr_2SO_2CBr_3$ | Stab.-1 |
| $CH_3(CH_2)_3CBr_2SO_2CBr_3$ | Stab.-2 |
| $CH_3(CH_2)_5CBr_2SO_2CBr_3$ | Stab.-3 |
| $CH_3(CH_2)_7CBr_2SO_2CBr_3$ | Stab.-4 |
| $CH_3(CH_2)_9CBr_2SO_2CBr_3$ | Stab.-5 |
| $Br_3CSO_2CBr_3$ | Stab.-6 |
| $Br_3CSO_2CBr_2(CH_2)_2CBr_2SO_2CBr_3$ | Stab.-7 |
| $Br_3CSO_2CBr_2(CH_2)_3CBr_2SO_2CBr_3$ | Stab.-8 |
| $Br_3CSO_2CBr_2(CH_2)_4CBr_2SO_2CBr_3$ | Stab.-9 |
| $Br_3CSO_2CBr_2(CH_2)_8CBr_2SO_2CBr_3$ | Stab.-10 |
| $(CH_3)_2CHSO_2CBr_3$ | Stab.-11 |
| $(CH_3)C(OCH_3)_2CH_2SO_2CBr_3$ | Stab.-12 |
| $CH_3CH_2C(CH_3)(Br)SO_2CBr_3$ | Stab.-13 |

Stability Test Results

The polybromoalkylsulfone molecules were tested as post-processing stabilizers (antifoggants) in two photothermographic silver formulations; a dry silver "green sensitive paper" formulation and a dry silver "infrared sensitive film" formulation.

Dry Silver Green Sensitive Paper

For the dry silver green sensitive paper each polybromoalkylsulfone stabilizer was added to a topcoat spread onto a green sensitive dry silver coating formulation.

The green sensitive dry silver formulation was prepared as described below.

The following steps were carried out in a thermostatted bath at 70 ° F. under red safe lights:

A 13.6 wt % solution of silver behenate/behenic acid half soap (201.5 g) was weighed out into a 450 ml. teflon coated beaker. Butvar B-76 TM (1.12 g) was added and the mixture was stirred 30 minutes more. Three 1.00 ml aliquots of a solution of 10.00 g zinc bromide in 100.0 ml methanol were added sequentially with stirring for 10 minutes after each addition. Toluene (66.66 g) was added and the mixture was stirred for an additional 15 minutes. A 2.40 ml aliquot of a solution of 4.00 g of pyridine in 100 ml methyl ethyl ketone was added with continued stirring for 15 minutes. The mixture was allowed to stand for 4 hours at 70° F.

Butvar B-76 TM (31.75 g) was added to the mixture which was then stirred for 30 minutes. An aliquot (2.73 ml) of a solution of 1.33 g N-bromosuccinimide in 100 ml methanol was added and stirring was continued for 30 minutes. The mixture was gently stirred overnight at 60° F.

CAO-05 TM (4.20 g, an antioxidant purchased from Rohm and Haas Co., Philadelphia, Pa.) was added with stirring for 5 minutes. Acryloid 21 TM (27.22 g, also from Rohm and Haas) was added with stirring for 5 minutes.

The following steps were carried out in a thermostatted bath at 60° F. (15.5° C.) under green safe lights.

A 6.00 ml aliquot of a solution of 0.03 g Dye-2, 25.00 ml methanol, and 75 ml toluene was added and the mixture was stirred for 5 minutes. The viscosity of the resultant solution should be between 180 and 220 centipoise. If greater than 220 centipoise then 7.00 ml acetone should be added to bring the viscosity into the appropriate range.

The silver trip formulation was coated at 4.4 mils (112 $\mu$m) at a coating weight of 1.25 gm/ft$^2$ onto paper and dried at 180 ° F. for one minute.

A topcoat solution was coated onto the coated samples prepared above. It was prepared by mixing: 164.728 g acetone, 82.350 g methyl ethyl ketone, 33.300 g methanol, 13.500 g C.A. 398-6 (a cellulose acetate, Eastman Kodak), 1.680 g Syloid 74X6000 (silica, Davison Chemical), 1.542 g phthalazine, 1.068 g 4-methylphthalic acid, 0.636 g tetrachlorophthalic acid, and 0.60 g of stabilizer compound.

The topcoat formulation was coated at 2.8 mils at a coating weight of 0.24 gm/ft$^2$ on top of silver emulsion.

All the compounds listed in Table I were tested in the dry silver paper topcoat formulation at concentration levels of 0.1 wt %, 0.2 wt %, 0.4 wt %, and 0.6 wt % and development conditions of 3 sec/290° F., 6 sec/250° F., 6 sec/260° F., and 12 sec/ 245° F. The developed samples were kept at ambient light exposure of 70 to 75 ft-candles. $D_{min}$ for each sample was measured on a weekly basis, and compared to a control containing 2-tribromomethylsulfonyl-benzothiazole (2-TBMBz) as a stabilizer. This material is a preferred stabilizer as described in U.S. Pat. No. 3,874,946.

Tables 2-6, demonstrate that the compounds of this invention are as good or better than a preferred compound of the art (2-TBMBz). In all of the tables, contrast is the angle in degrees (from the horizontal) of the D log E curve.

The green sensitive coated paper was imaged by exposing with a photometric sensitometer with an Eastman Kodak #101 tungsten light source. After exposure, the film strips (25 mm $\times$ 8 inches) were processed at 250° F. (121 ° C.) by heating for 6 seconds in a hot roll processor. The images obtained were evaluated by a computer densitometer. Sensitometric results include $D_{min}$, $D_{max}$, speed, and contrast. In these samples, the lower the speed number, the "faster" the paper. Sensitometry of unimaged material was also evaluated following accelerated aging at 120° F. and 50% relative humidity for 7, 14, 21, and 28 days.

Table 2 compares Stabilizer-4 of this invention with 2-TBMBz in the green sensitive dry silver paper formulation prepared above. Stabilizer-4 was present at 0.20% in the topcoat. 2-TBMBz was present at 0.60% in the topcoat. Both samples were processed at 250° F. for 6 seconds.

Table 3 compares Stabilizer-9 of this invention with 2-TBMBz in the green sensitive dry silver paper formulation prepared above. Stabilizer 9 was present at 0.20% in the topcoat. 2-TBMBz was present at 0.60% in the topcoat. Both samples were processed at 250° F. for 6 seconds.

Table 4 compares Stabilizer-2 of this invention with 2-TBMBz in the green sensitive dry silver paper formulation prepared above. Stabilizer-2 was present at 0.20% in the topcoat. 2-TBMBz was present at 0.60% in the topcoat. Both samples were processed at 250° F. for 6 seconds.

Table 5 compares Stabilizer-13 of this invention with 2-TBMBz in the green sensitive dry silver paper formulation prepared above. Stabilizer-13 was present at 0.20% in the topcoat. 2-TBMBz was present at 0.60% in the topcoat. Both samples were processed at 250° F. for 6 seconds.

Print stability of imaged material was also evaluated. Table 6 compares the print stability over 24 weeks of the green sensitive dry silver paper formulation prepared above incorporating Stabilizers 4, 9, 2, and 13, with 2-TBMBz. Again the stabilizers of this invention campare favorably with 2-TBMBz.

Dry Silver Infrared Sensitive Film

For the infrared sensitive dry silver formulation, each polybromoalkylsulfone stabilizer was added to the infrared sensitive dry silver coating formulation. The preparation of this infrared sensitive dry silver formulation is as follows:

Silver halide-silver behenate dry soap was prepared by the procedures of U.S. Pat. No. 3,839,049. The silver halide totaled 9 wt % of the total silver and the silver behenate was 91 wt % of the total silver. The silver halide was a 50/50 mixture of preformed silver halide grains. Both had a composition of 2% iodide and bromide and were mono-dispersed. The two silver bromo-iodide emulsions had grain sizes of 0.055 and 0.07 microns.

A photothermographic emulsion was prepared by homogenizing 300 g of the silver halide-silver behenate dry soap with 525 g toluene, 1675 g 2-butanone, and 50 g polyvinyl butyral (Butvar B-76, Monsanto). The homogenized emulsion (500 g) and 100 g 2-butanone were cooled to 13° C. with stirring. 75.7 g additional polyvinyl butyral (Butvar B-76) was added and stirred for 20 minutes. Pyridinium hydrobromide perbromide (0.45 g) was added and stirred for two hours. The addition of 3.25 ml of calcium bromide solution (1 g of $CaBr_2$ and 10 ml of methanol) was followed by 30 minutes of stirring. The temperature was raised to 21 ° C. and the following were added in 15 minute increments with stirring: 3 g of 2-(4-chlorobenzoyl)benzoic acid, IR dye solution (8.8 mg of Dye-1 in 7.1 g of DMF), 0.15 g of 2-mercaptobenzimidazole, and 16.6 g of 1,1-bis(2-hydroxy-3,5-dimethylphenyl)-3,5,5-trimethylhexane.

Each stabilizer was added to the formulation described above, in amounts of 0.13%, 0.19%, and 0.26% by weight. Each sample was measured for sensitometry after coating as described below and after aging for one and two weeks at 49° C. and 50% relative humidity.

The photothermographic emulsion was coated on 3 mil (76μm) polyester base by means of a knife coater and dried at 175° F. for four minutes. The dry coating weight was 23 g/m$^2$.

An active, protective topcoat solution was prepared with the following ingredients:

256.0 g acetone
123.0 g 2-butanone
50.0 g methanol
20.2 g cellulose acetate
2.89 g phthalazine
1.55 g 4-methylphthalic acid
1.01 g tetrachlorophthalic acid
0.90 g tetrabromophthalic anhydride
1.50 g tetrachlorophthalic anhydride The topcoat solutions were coated over the silver layer at a dry weight of 3.0 g/m$^2$. The layer was dried at 165° F. for four minutes.

The infrared sensitive coated film was imaged by exposure at 780 nm with a laser diode sensitometer. After exposure, the film strips (35 mm × 8 inches) were processed at 260° F. for 10 seconds in a hot roll processor. The images obtained were evaluated by a computer densitometer. Sensitometric results include $D_{min}$, $D_{max}$, speed, and contrast. In these samples the higher the speed number, the faster the film.

Tables 7 and 8 compare Stabilizers 1 and 13 of this invention with 2-TBMBz in the infrared sensitive dry silver film formulation prepared above. The amount of stabilizer present is in grams of stabilizer per 39 g of silver photothermographic emulsion. All samples were processed at 260° F. (126° C.) for 10 seconds.

TABLE 2

| | Comparison of Stabilizer-4 with 2-TBMBz in Green Sensitive Paper | | | | | | | |
|---|---|---|---|---|---|---|---|---|
| No. of | $D_{min}$ | | $D_{max}$ | | Speed | | Contrast Angle | |
| days | Stab. 4 | 2-TBMBz | Stab. 4 | 2-TBMBz | Stab. 4 | 2-TBMBz | Stab. 4 | 2-TBMBz |
| Inital | 0.1 | 0.11 | 1.63 | 1.63 | 1.06 | 1.03 | 67.6° | 66.9° |
| 7 | 0.09 | 0.10 | 1.59 | 1.58 | 1.15 | 1.11 | 65.0° | 63.6° |
| 14 | 0.09 | 0.09 | 1.56 | 1.54 | 1.20 | 1.16 | 63.3° | 62.7° |
| 21 | 0.09 | 0.09 | 1.57 | 1.54 | 1.28 | 1.28 | 55.9° | 54.0° |
| 28 | 0.11 | 0.10 | 1.50 | 1.50 | 1.49 | 1.50 | 41.1° | 43.8° |

TABLE 3

| | Comparison of Stabilizer-9 with 2-TBMBz in Green Sensitive Paper | | | | | | | |
|---|---|---|---|---|---|---|---|---|
| No. of | $D_{min}$ | | $D_{max}$ | | Speed | | Contrast Angle | |
| days | Stab. 9 | 2-TBMBz | Stab. 9 | 2-TBMBz | Stab. 9 | 2-TBMBz | Stab. 9 | 2-TBMBz |
| Inital | 0.114 | 0.117 | 1.63 | 1.63 | 1.07 | 1.02 | 67.1° | 66.3° |
| 7 | 0.087 | 0.093 | 1.58 | 1.56 | 1.26 | 1.16 | 62.2° | 61.4° |

TABLE 3-continued
Comparison of Stabilizer-9 with 2-TBMBz in Green Sensitive Paper

| No. of days | $D_{min}$ Stab. 9 | $D_{min}$ 2-TBMBz | $D_{max}$ Stab. 9 | $D_{max}$ 2-TBMBz | Speed Stab. 9 | Speed 2-TBMBz | Contrast Angle Stab. 9 | Contrast Angle 2-TBMBz |
|---|---|---|---|---|---|---|---|---|
| 14 | 0.087 | 0.093 | 1.55 | 1.52 | 1.34 | 1.23 | 59.2° | 58.2° |

TABLE 4
Comparison of Stabilizer-2 with 2-TBMBz in Green Sensitive Paper

| No. of days | $D_{min}$ Stab. 2 | $D_{min}$ 2-TBMBz | $D_{max}$ Stab. 2 | $D_{max}$ 2-TBMBz | Speed Stab. 2 | Speed 2-TBMBz | Contrast Angle Stab. 2 | Contrast Angle 2-TBMBz |
|---|---|---|---|---|---|---|---|---|
| Inital | 0.11 | 0.12 | 1.63 | 1.63 | 1.05 | 1.01 | 66.7° | 66.4° |
| 7 | 0.09 | 0.09 | 1.58 | 1.58 | 1.12 | 1.06 | 64.0° | 62.6° |
| 14 | 0.08 | 0.08 | 1.57 | 1.55 | 1.11 | 1.08 | 61.9° | 60.6° |
| 21 | 0.08 | 0.09 | 1.54 | 1.52 | 1.26 | 1.18 | 55.5° | 57.8° |
| 28 | 0.13 | 0.09 | 1.55 | 1.53 | 1.43 | 1.34 | 46.0° | 49.0° |

TABLE 5
Comparison of Stabilizer-13 with 2-TBMBz in Green Sensitive Paper

| No. of days | $D_{min}$ Stab. 13 | $D_{min}$ 2-TBMBz | $D_{max}$ Stab. 13 | $D_{max}$ 2-TBMBz | Speed Stab. 13 | Speed 2-TBMBz | Contrast Angle Stab. 13 | Contrast Angle 2-TBMBz |
|---|---|---|---|---|---|---|---|---|
| Inital | 0.11 | 0.13 | 1.63 | 1.45 | 1.01 | 1.00 | 66.5° | 66.4° |
| 7 | 0.09 | 0.10 | 1.55 | 1.56 | 1.11 | 1.08 | 61.6° | 62.3° |
| 14 | 0.09 | 0.09 | 1.54 | 1.56 | 1.16 | 1.16 | 57.2° | 58.9° |
| 21 | 0.10 | 0.09 | 1.53 | 1.53 | 1.32 | 1.36 | 48.9° | 51.4° |
| 28 | 0.17 | 0.11 | 1.50 | 1.50 | 1.65 | 1.61 | 40.3° | 42.8° |

TABLE 6
Comparison of Print Stability of Stabilizers with 2-TBMBz in Green Sensitive Paper

| No. of Weeks | Stab. 4 | Stab. 9 | Stab. 2 | Stab. 13 | 2-TBMBz |
|---|---|---|---|---|---|
| Inital | 0.10 | 0.11 | 0.11 | 0.11 | 0.11 |
| 1 | 0.13 | 0.15 | 0.14 | 0.13 | 0.12 |
| 2 | 0.13 | 0.15 | 0.15 | 0.14 | 0.12 |
| 3 | 0.13 | 0.16 | 0.15 | 0.14 | 0.13 |
| 4 | 0.14 | 0.16 | 0.16 | 0.14 | 0.13 |
| 6 | 0.15 | 0.16 | 0.16 | 0.14 | 0.13 |
| 8 | 0.16 | 0.17 | 0.16 | 0.13 | 0.13 |
| 12 | 0.17 | 0.18 | 0.17 | 0.14 | 0.13 |
| 16 | 0.18 | 0.20 | 0.17 | 0.13 | 0.14 |
| 21 | 0.20 | 0.20 | 0.17 | 0.15 | 0.18 |
| 24 | 0.21 | 0.21 | 0.18 | 0.15 | 0.18 |

TABLE 7
Comparison of Stabilizer-1 with 2-TBMBz in Infrared Film

| Stab. Conc'n | $D_{min}$ Stab. 1 | $D_{min}$ 2-TBMBz | $D_{max}$ Stab. 1 | $D_{max}$ 2-TBMBz | Speed Stab. 1 | Speed 2-TBMBz | Contrast Angle Stab. 1 | Contrast Angle 2-TBMBz |
|---|---|---|---|---|---|---|---|---|
| 0.05 | 0.108 | 0.127 | 2.79 | 2.87 | 2.63 | 2.98 | 69.3° | 71.8° |
| 0.075 | 0.107 | 0.113 | 2.63 | 2.84 | 2.70 | 2.94 | 71.2° | 71.0° |
| 0.10 | 0.100 | 0.109 | 2.55 | 2.89 | 2.59 | 2.88 | 70.2° | 71.4° |

TABLE 8
Comparison of Stabilizer-13 with 2-TBMBz in Infrared Film

| Stab. Conc'n | $D_{min}$ Stab. 1 | $D_{min}$ 2-TBMBz | $D_{max}$ Stab. 1 | $D_{max}$ 2-TBMBz | Speed Stab. 1 | Speed 2-TBMBz | Contrast Angle Stab. 1 | Contrast Angle 2-TBMBz |
|---|---|---|---|---|---|---|---|---|
| 0.05 | 0.110 | 0.127 | 2.82 | 2.87 | 2.86 | 2.98 | 70.7° | 71.8° |
| 0.075 | 0.104 | 0.113 | 2.77 | 2.84 | 2.87 | 2.94 | 70.2° | 71.0° |
| 0.10 | 0.098 | 0.109 | 2.70 | 2.89 | 2.81 | 2.88 | 70.3° | 71.4° |

Reasonable variations and modifications are possible from the foregoing disclosure without departing from either the spirit or scope of the present invention as defined in the claims.

What is claimed is:

1. A photothermographic article comprising a photothermographic composition coated on a substrate wherein said photothermographic composition comprises:
  (a) light-sensitive silver halide;
  (b) a light-insensitive organic silver salt;
  (c) a reducing agent for the light-insensitive organic silver salt; and
  (d) an antifoggant of the formula:

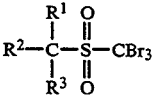

wherein: $R^1$, $R^2$, and $R^3$ are $-(CH_2)_y SO_2 CBr_3$ wherein y is an integer from 0 to 22 inclusive.

2. A photothermographic article comprising a photothermographic composition coated on a substrate wherein said photothermographic composition comprises:
  (a) light-sensitive silver halide;
  (b) a light-insensitive organic silver salt;

(c) a reducing agent for the light-insensitive organic silver salt; and
(d) an antifoggant of the formula:

$$CH_3-(CH_2)_n-CBr_2SO_2CBr_3$$

wherein n is an integer from 1 to 22 inclusive.

3. The photothermographic article according to claim 2 wherein n is an integer from 2 to 6 inclusive.

4. The photothermographic article according to claim 3 wherein n is 2.

5. A photothermographic article comprising a photothermographic composition coated on a substrate wherein said photothermographic composition comprises:
(a) light-sensitive silver halide;
(b) a light-insensitive organic silver salt;
(c) a reducing agent for the light-insensitive organic silver salt; and
(d) an antifoggant of the formula:

$$Br_3CSO_2CBr_2-(CH_2)_y CBr_2SO_2CBr_3$$

wherein y is an integer from 0 to 22 inclusive.

6. The photothermographic article according to claim 5 wherein y is an integer from 2 to 7 inclusive.

7. The photothermographic article according to claim 6 wherein y is 2.

* * * * *